United States Patent
Yamanoi et al.

(10) Patent No.: US 9,006,273 B2
(45) Date of Patent: Apr. 14, 2015

(54) N-HETERO-RING-SUBSTITUTED AMIDE DERIVATIVE

(75) Inventors: Shigeo Yamanoi, Yokosuka (JP); Madoka Hatta, Koto-ku (JP); Hidenori Namiki, Yokohama (JP); Koji Matsumoto, Machida (JP); Tomomi Yoshitomi, Kawasaki (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/235,331

(22) PCT Filed: Jul. 27, 2012

(86) PCT No.: PCT/JP2012/069098
§ 371 (c)(1),
(2), (4) Date: Jan. 27, 2014

(87) PCT Pub. No.: WO2013/018675
PCT Pub. Date: Feb. 7, 2013

(65) Prior Publication Data
US 2014/0221437 A1 Aug. 7, 2014

(30) Foreign Application Priority Data

Jul. 29, 2011 (JP) .................................. 2011-166248

(51) Int. Cl.
*C07D 413/12* (2006.01)

(52) U.S. Cl.
CPC .................................... *C07D 413/12* (2013.01)

(58) Field of Classification Search
None
See application file for complete search history.

(56) References Cited

U.S. PATENT DOCUMENTS

| 8,377,923 | B2 | 2/2013 | Yoshimura |
| 8,557,802 | B2 | 10/2013 | Yamanoi |
| 2013/0217733 | A1 | 8/2013 | Yamanoi |

FOREIGN PATENT DOCUMENTS

| WO | 97/46556 A1 | 12/1997 |
| WO | 02/46174 A1 | 6/2002 |
| WO | 2005/061489 A1 | 7/2005 |
| WO | 2007/003960 A1 | 1/2007 |
| WO | 2007/003962 A2 | 1/2007 |
| WO | 2007/116229 A1 | 10/2007 |
| WO | 2008/130370 A1 | 10/2008 |
| WO | 2010/001946 A1 | 1/2010 |
| WO | 2011/016469 A1 | 2/2011 |
| WO | 2012/050151 A1 | 4/2012 |

OTHER PUBLICATIONS

International Search Report and Written Opinion mailed Oct. 9, 2012, issued in corresponding International Application No. PCT/JP2012/069098, filed Jul. 27, 2012, 8 pages.
International Preliminary Report on Patentability mailed Feb. 4, 2014, issued in corresponding International Application No. PCT/JP2012/069098, filed Jul. 27, 2012, 6 pages.
Search Report mailed Dec. 5, 2014, issued in corresponding Chinese Application No. 201280047243X, filed Jul. 27, 2012, 2 pages.

*Primary Examiner* — Sun Jae Yoo
(74) *Attorney, Agent, or Firm* — Christensen O'Connor Johnson Kindness PLLC

(57) ABSTRACT

Compounds having an excellent hypoglycemic effect and β cell- or pancreas-preserving effects or pharmaceutically acceptable salts thereof, and a pharmaceutical composition having an excellent therapeutic effect and/or prophylactic effect on type 1 diabetes, type 2 diabetes, and the like, which cause hyperglycemia due to abnormal glucose metabolism. A compound represented by general formula (I), or a pharmaceutically acceptable salt thereof, is disclosed.

(I)

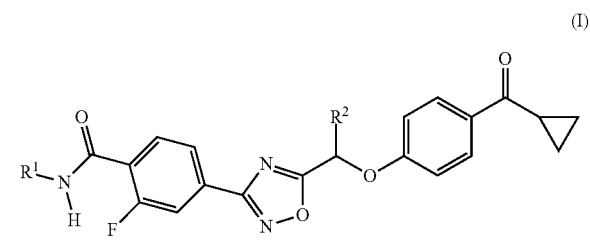

14 Claims, No Drawings

N-HETERO-RING-SUBSTITUTED AMIDE DERIVATIVE

TECHNICAL FIELD

The present invention relates to novel N-hetero-ring-substituted amide derivatives which have a hypoglycemic effect and/or β cell- or pancreas-protecting effects, or pharmacologically acceptable salts thereof, and pharmaceutical compositions containing those active ingredients.

BACKGROUND ART

Diabetes mellitus is a metabolic disease primarily characterized by a chronic hyperglycemic state due to impaired insulin action. The treatment of diabetes is generally performed by drug therapy together with diet and exercise therapy. Examples of oral anti-diabetic agents include biguanides and thiazolidinediones that improve insulin resistance; sulfonylureas and glinides that promote insulin secretion from pancreatic β cells; and α-glucosidase inhibitors that inhibit sugar absorption.

However, it is reported that they have side effects: biguanides produce gastrointestinal symptoms and lactic acidosis; thiazolidinediones produce weight gain and edema; sulfonylureas and glinides produce hypoglycemia or secondary failure due to long-term use; and α-glucosidase inhibitors produce diarrhea etc. Therefore, development of an oral hypoglycemic agent which can address such problems is desired.

In recent years, piperidine compounds have been developed as oral anti-diabetic agents having new structures. (see, for example, Patent Literature 1 to 4).

CITATION LIST

Patent Literature

Patent Literature 1: WO 2007/116229
Patent Literature 2: WO 2007/003960
Patent Literature 3: WO 2007/003962
Patent Literature 4: WO 2005/061489
Patent Literature 5: WO 2011/016469
Patent Literature 6: WO 2012/050151

SUMMARY OF THE INVENTION

Problems to be Solved by the Invention

However, the compounds described in the above patent literature 1 to 4, have an insufficient hypoglycemic effect and insufficient β cell- or pancreas-protecting effects. Furthermore, the present invention is neither described nor suggested in the above patent literature 1 to 6. Thus, an object of the present invention is to provide a compound which has a new structure that is neither described nor suggested in the above patent literature and has an excellent hypoglycemic effect and a β cell- or pancreas-protecting effect, or a pharmaceutically acceptable salt thereof; a pharmaceutical composition having an excellent therapeutic effect and/or prophylactic effect on type 1 diabetes, type 2 diabetes and the like, which cause an increase in blood sugar levels due to abnormal glucose metabolism; and a pharmaceutical composition having a β cell- or pancreas-protecting effect.

Means for Solving the Problems

The present invention provides:
(1) a compound represented by general formula (I):

[Chemical Formula 1]

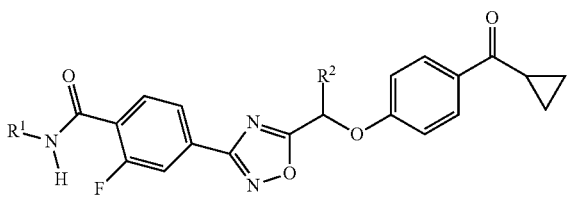

(I)

wherein
$R^1$ represents

[Chemical Formula 2]

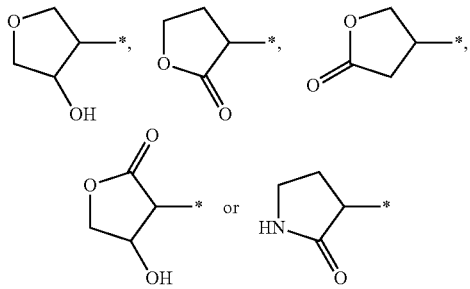

* represents a binding site with a nitrogen atom, and
R2 represents a methyl group or an ethyl group; or a pharmaceutically acceptable salt thereof;

(2) a compound selected from the group consisting of the following compounds:

4-(5-{(1R)-1-[4-(cyclopropylcarbonyl)phenoxy]propyl}-1,2,4-oxadiazol-3-yl)-2-fluoro-N-[(3S,4R)-4-hydroxytetrahydrofuran-3-yl]benzamide;

4-(5-{(1R)-1-[4-(cyclopropylcarbonyl)phenoxy]propyl}-1,2,4-oxadiazol-3-yl)-2-fluoro-N-[(3R,4S)-4-hydroxytetrahydrofuran-3-yl]benzamide;

4-(5-{(1R)-1-[4-(cyclopropylcarbonyl)phenoxy]ethyl}-1,2,4-oxadiazol-3-yl)-2-fluoro-N-[(3R,4S)-4-hydroxytetrahydrofuran-3-yl]benzamide;

4-(5-{(1R)-1-[4-(cyclopropylcarbonyl)phenoxy]ethyl}-1,2,4-oxadiazol-3-yl)-2-fluoro-N-[(3S,4R)-4-hydroxytetrahydrofuran-3-yl]benzamide;

4-(5-{(1R)-1-[4-(cyclopropylcarbonyl)phenoxy]propyl}-1,2,4-oxadiazol-3-yl)-2-fluoro-N-[(3R)-2-oxotetrahydrofuran-3-yl]benzamide;

4-(5-{(1R)-1-[4-(cyclopropylcarbonyl)phenoxy]propyl}-1,2,4-oxadiazol-3-yl)-2-fluoro-N-[(3S)-2-oxotetrahydrofuran-3-yl]benzamide;

4-(5-{(1R)-1-[4-(cyclopropylcarbonyl)phenoxy]propyl}-1,2,4-oxadiazol-3-yl)-2-fluoro-N-[(3S)-5-oxotetrahydrofuran-3-yl]benzamide;

4-(5-{(1R)-1-[4-(cyclopropylcarbonyl)phenoxy]propyl}-1,2,4-oxadiazol-3-yl)-2-fluoro-N-[(3R)-2-oxopyrrolidin-3-yl]benzamide;

4-(5-{(1R)-1-[4-(cyclopropylcarbonyl)phenoxy]propyl}-1,2,4-oxadiazol-3-yl)-2-fluoro-N-[(3S)-2-oxopyrrolidin-3-yl]benzamide;

4-(5-{(1R)-1-[4-(cyclopropylcarbonyl)phenoxy]propyl}-1,2,4-oxadiazol-3-yl)-2-fluoro-N-[(3S,4S)-4-hydroxy-2-oxotetrahydrofuran-3-yl]benzamide;

4-(5-{(1R)-1-[4-(cyclopropylcarbonyl)phenoxy]ethyl}-1,2,4-oxadiazol-3-yl)-2-fluoro-N-[(3R)-2-oxopyrrolidin-3-yl]benzamide;

4-(5-{(1R)-1-[4-(cyclopropylcarbonyl)phenoxy]ethyl}-1,2,4-oxadiazol-3-yl)-2-fluoro-N-[(3S)-2-oxopyrrolidin-3-yl]benzamide;

4-(5-{(1R)-1-[4-(cyclopropylcarbonyl)phenoxy]propyl}-1,2,4-oxadiazol-3-yl)-2-fluoro-N-[(3S,4R)-4-hydroxy-2-oxotetrahydrofuran-3-yl]benzamide;

4-(5-{(1R)-1-[4-(cyclopropylcarbonyl)phenoxy]ethyl}-1,2,4-oxadiazol-3-yl)-2-fluoro-N-[(3R,4R)-4-hydroxytetrahydrofuran-3-yl]benzamide; and 4-(5-{(1R)-1-[4-(cyclopropylcarbonyl)phenoxy]ethyl}-1,2,4-oxadiazol-3-yl)-2-fluoro-N-[(3S,4S)-4-hydroxytetrahydrofuran-3-yl]benzamide;

or a pharmaceutically acceptable salt thereof;

(3) a pharmaceutical composition containing, as an active ingredient, a compound as set forth in item (1) or (2), or a pharmaceutically acceptable salt thereof;

(4) a pharmaceutical composition as set forth in item (3), for treating type 1 diabetes, type 2 diabetes, or obesity;

(5) a pharmaceutical composition as set forth in item (3), for protecting β cells or the pancreas;

(6) use of a compound as set forth in item (1) or (2) or a pharmaceutically acceptable salt thereof, for preparing a pharmaceutical composition;

(7) use of a compound, as set forth in item (6), for treating type 1 diabetes, type 2 diabetes, or obesity, or for protecting β cells or the pancreas;

(8) a method for treating a disease, the method including administering to a mammal a compound as set forth in item (1) or (2) or a pharmaceutically acceptable salt thereof;

(9) a method for treating a disease as set forth in item (8), wherein the disease is type 1 diabetes, type 2 diabetes, or obesity;

(10) a method for protecting β cells or the pancreas, the method including administering to a mammal a compound as set forth in item (1) or (2) or a pharmaceutically acceptable salt thereof; and

(11) a method as set forth in item (8), wherein the mammal is a human being.

Effects of the Invention

The present invention provides an N-hetero-ring-substituted amide derivative having an excellent hypoglycemic effect, and a β cell- or pancreas-protecting effect, or a pharmaceutically acceptable salt thereof, a pharmaceutical composition having an excellent therapeutic effect and/or prophylactic effect on type 1 diabetes, type 2 diabetes and the like due to hyperglycemia, and a pharmaceutical composition having a β cell- or pancreas-protecting effect.

BEST MODES FOR CARRYING OUT THE INVENTION

A "pharmaceutically acceptable salt" as used in the present specification means a salt formed by allowing the compound of the present invention to react with an acid or a base.

Examples of the salt include hydrohalogenic acid salts such as hydrofluorides, hydrochlorides, hydrobromides, and hydroiodides; inorganic acid salts such as hydrochlorides, nitrates, perchlorates, sulfates and phosphates; lower alkanesulfonic acid salts such as methanesulfonates, trifluoromethanesulfonates, and ethanesulfonates; arylsulfonic acid salts such as benzenesulfonates, and p-toluenesulfonates; organic acid salts such as acetates, malates, fumarates, succinates, citrates, ascorbates, tartrates, oxalates, and maleates; alkali metal salts such as sodium salts, potassium salts, and lithium salts; alkaline earth metal salts such as calcium salts and magnesium salts; metal salts such as aluminum salts and iron salts; inorganic salts such as ammonium salts; amine salts including organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates.

The compound of the present invention absorbs water when, for example, left to stand in the atmosphere, so that the absorbed water can adhere to the compound and a hydrate may be formed. Therefore, such a hydrate is also included in the concept of the salt of the present invention.

Since the compound of the present invention may have asymmetric carbon atoms in the molecule, the compound has optical isomers. These isomers and mixtures of these isomers are all represented by a single formula, that is, the general formula (I). Therefore, the present invention encompasses all of the optical isomers of the compound represented by the general formula (I), and mixtures of these optical isomers at any ratios. Such an optical isomer can be produced by, for example, using raw materials having optical activity instead of the raw materials used in the production methods, Reference Examples and Examples that will be described below, or can be obtained by subjecting a compound that has been produced by making reference to the production methods, Reference Examples, Examples and the like that will be described below, to an optical resolution method that is known in the pertinent art, for example, a diastereomer method, an enzymatic reaction method, or an optical resolution method based on chromatography.

The present invention may also encompass compounds in which one or more of the atoms constituting the compound represented by the general formula (I) have been substituted with isotopes of the atoms. Isotopes include the two classes of radioactive isotopes and stable isotopes, and examples of the isotopes include, for example, isotopes of hydrogen ($^2$H and $^3$H), isotopes of carbon ($^{11}$C, $^{13}$C and $^{14}$C) isotopes of nitrogen ($^{13}$N and $^{15}$N), isotopes of oxygen ($^{15}$O, $^{17}$O and $^{18}$O), and isotopes of fluorine ($^{18}$F). A composition containing a compound labeled with an isotope is useful as, for example, a therapeutic agent, a prophylactic agent, a research reagent, an assay reagent, a diagnostic agent, or an in vivo diagnostic imaging agent. Compounds labeled with isotopes and mixtures of compounds labeled with isotopes at any ratios are all included in the present invention. A compound labeled with an isotope can be produced by a method that is known in the pertinent art, for example, using raw materials labeled with isotopes instead of the raw materials used in the production methods that will be described below.

The present invention may also encompass prodrugs of the compound represented by the general formula (I). A prodrug is a derivative of the compound represented by the general formula (I), and means a compound which is enzymatically or chemically converted to the compound of the present invention in the living body.

Examples of a prodrug include compounds in which an amino group in the molecule has been acylated, alkylated or phosphorylated; compounds in which a carboxyl group in the molecule has been esterified or amidated; and compounds in which a hydroxyl group in the molecule has been acylated, alkylated or phosphorylated (see, for example, Povl Krogsgaard-Larsen, et al., "A Textbook of Drug Design and Development", Second Edition, Harwood Academic Publishers, 1996, pp. 351-385). Such a prodrug can be produced from the compound represented by the general formula (I) by a method known in the pertinent art.

The compound of the present invention can be easily produced from known compounds according to the Reference Examples and Examples that will be described below.

The compound of the present invention or a pharmaceutically acceptable salt thereof obtained by the methods described above has an excellent hypoglycemic effect, and can therefore be used as an active ingredient of a pharmaceutical composition that can be used in the treatment and/or prevention of type 1 diabetes, type 2 diabetes, gestational diabetes, hyperglycemia due to other factors, impaired glucose tolerance (IGT), obesity, diabetes-associated diseases (for example, hyperlipidemia, hypercholesterolemia, abnormal lipid metabolism, hypertension, fatty liver, metabolic syndrome, edema, heart failure, angina pectoris, myocardial infarction, arteriosclerosis, hyperuricemia, and gout), or diabetic complications (for example, retinosis, kidney failure, neuropathy, cataract, gangrenous leg, infections, and ketosis).

Furthermore, the compound of the present invention or a pharmaceutically acceptable salt thereof has an excellent β cell- or pancreas-protecting effect, and can therefore be used as an active ingredient of a pharmaceutical composition that can be used to protecting β cells or the pancreas.

The compound of the present invention can also be used in combination with a therapeutic drug for diabetes other than the compound of the present invention, a therapeutic drug for diabetic complications, hyperlipidemia, hypertension, and the like.

When a pharmaceutical composition containing the compound of the present invention or a pharmaceutically acceptable salt thereof is administered to a mammal (for example, human, horse, cow or pig; preferably a human being), the pharmaceutical composition can be administered systemically or topically, and orally or parenterally.

Appropriate dosage forms of the pharmaceutical composition of the present invention can be selected in accordance with the administration mode. The pharmaceutical composition of the present invention can be prepared according to the preparation methods for various conventionally used formulations.

Examples of the dosage form of the pharmaceutical composition for oral use include tablets, pills, powders, granules, capsules, liquids, suspensions, emulsions, syrups, and elixirs. Pharmaceutical compositions of such dosage forms can be prepared according to conventional methods, by appropriately selecting as necessary, excipients, binders, disintegrants, lubricating agents, swelling agents, swelling aids, coating agents, plasticizers, stabilizers, antiseptics, antioxidants, colorants, dissolution aids, suspending agents, emulsifiers, sweeteners, preservatives, buffers, diluents, wetting agents and the like, which are conventionally used as additives.

Examples of the dosage forms of a pharmaceutical composition for parenteral use include injections, ointments, gels, creams, poultices, patches, aerosols, inhalants, sprays, eye drops, nose drops, and suppositories. Pharmaceutical compositions of such dosage forms can be prepared according to conventional methods, by appropriately selecting as necessary, stabilizers, antiseptics, dissolution aids, moisturizers, preservatives, antioxidants, fragrances, gelling agents, neutralizing agents, buffers, isotonic agents, surfactants, colorants, buffering agents, thickeners, wetting agents, fillers, absorption promoting agents, suspending agents, binders, and the like, which are conventionally used as additives.

The administration amount of the compound of the present invention or a pharmaceutically acceptable salt thereof may vary with the symptoms, age, body weight or the like. However, in the case of oral administration, the compound or the salt is administered once or several times a day, in an amount of 1 to 2000 mg, and preferably 1 to 400 mg, in terms of the compound, per dose for an adult; and in the case of parenteral administration, the compound or the salt is administered once or several times a day, in an amount of 0.01 to 500 mg, and preferably 0.1 to 300 mg, in terms of the compound, per dose for an adult.

EXAMPLES

Hereinafter, the present invention will be described in more detail by way of Reference Examples, Examples, a Formulation Example and Test Examples, but the scope of the present invention is not intended to be limited to these.

Reference Example 1 tert-Butyl 4-cyano-2-fluorobenzoate

[Chemical Formula 3]

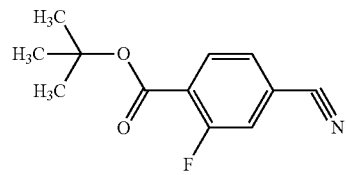

Di-tert-butyl dicarbonate (145.4 g, 666 mmol), and 4-dimethylaminopyridine (7.40 g, 60.6 mmol) were added to a tert-butyl alcohol (1000 mL)-tetrahydrofuran (500 mL) solution of 4-cyano-2-fluorobenzoate (100.0 g, 606 mmol), and the mixture was stirred at 60° C. for 3 hours. The reaction mixture was cooled to room temperature, and the insoluble material was removed by filtration through Celite. The solvent was distilled off under reduced pressure. Thus, a crude product of the title compound was obtained.

Reference Example 2 tert-Butyl 4-amino(hydroxyimino)methyl-2-fluorobenzoate

[Chemical Formula 4]

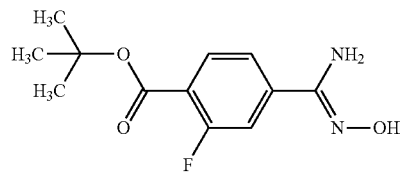

A 50% aqueous solution of hydroxylamine (60 mL, 100 mmol) was added to an ethanol (100 mL)-tetrahydrofuran (50 mL) solution of the compound obtained in Reference Example 1 (11.0 g, 66.6 mmol), and the mixture was stirred at 80° C. for 2 hours. The reaction mixture was cooled to room temperature, and then the solvent was distilled off under reduced pressure. The resulting residue was washed with water, and was dried at 40° C. for 2 days under reduced pressure. Thus, the title compound (150.0 g, yield: 98%) was obtained.

$^1$H-NMR (400 MHz, CDCl$_3$) δ ppm:
7.89 (1H, t, J=8 Hz), 7.44 (2H, dd, J=8, 2 Hz), 7.39 (2H, dd, J=11, 2 Hz), 4.90 (2H, s), 1.60 (9H, s).

Reference Example 3

Cyclopropyl(4-hydroxyphenyl)methanone

[Chemical Formula 5]

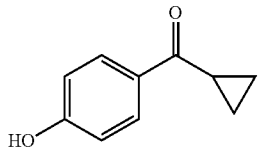

4-Chloropropyl(4-hydroxyphenyl)methanone (25.1 g, 127 mmol) was added to a 2 N aqueous solution of sodium hydroxide (283 mL, 566 mmol) in several portions under ice cooling. The reaction mixture was allowed to warm up to room temperature, and was stirred for 6 hours, and then dilute sulfuric acid (1.8 N) was added to the reaction mixture under ice cooling until a pH value of 2 was obtained. The reaction mixture was subjected to extraction twice with ethyl acetate. The organic layer thus obtained was washed with water and brine, and then was dried over anhydrous magnesium sulfate. The solvent was distilled off under reduced pressure, and the resulting residue was purified by silica gel column chromatography (hexane:ethyl acetate=4:1→2:1, v/v) to give the title compound (17.7 g, yield: 86%).

$^1$H-NMR (400 MHz, CDCl$_3$) δ ppm:
7.99-7.96 (2H, m), 6.93-6.89 (2H, m), 6.16 (1H, s), 2.67-2.61 (1H, m), 1.28-1.18 (2H, m), 1.09-0.97 (2H, m).

Reference Example 4

(2S)-2-Acetoxy butyric acid

[Chemical Formula 6]

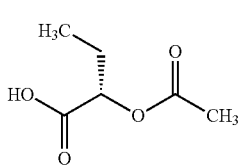

Sodium acetate (11.9 g, 146 mmol) and tert-butyl nitrite (15.0 g, 146 mmol) were added to an acetic acid (300 mL) solution of (2S)-2-aminobutyric acid (10.0 g, 97.0 mmol) under ice cooling, and was stirred at 60° C. for 2 hours. The reaction mixture was cooled to room temperature, and then the solvent was distilled off under reduced pressure. Water was added to the residue, and the mixture was subjected to extraction twice with ethyl acetate. The organic layer thus obtained was washed with water and brine, and then was dried over anhydrous sodium sulfate. The solvent was distilled off under reduced pressure. Furthermore, the residue was azeotropically boiled with 1,4-dioxane (50 mL) twice. Thus, the title compound (8.4 g, yield: 60%) was obtained.

$^1$H-NMR (400 MHz, CDCl$_3$) δ ppm:
5.00 (1H, m), 2.15 (3H, s), 1.94-1.90 (2H, m), 1.03 (3H, t, J=7 Hz);
MS (FAB) m/z: 147 [M+H]$^+$.

Reference Example 5 tert-Butyl 4-{5-[(1S)-1-acetoxypropyl]-1,2,4-oxadiazol-3-yl}-2-fluorobenzoate

[Chemical Formula 7]

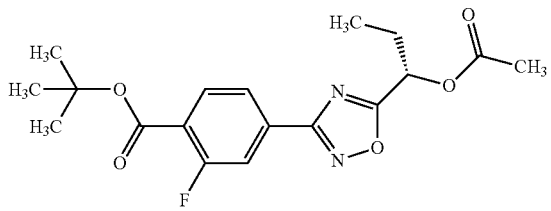

1-Hydroxybenzotriazole monohydrate (7.2 g, 53.0 mmol) and N-(3-dimethylaminopropyl)-N'-ethylcarbodiimide (20.3 g, 159 mmol) were added to an N,N-dimethylformamide (200 mL) solution of the compound obtained in Reference Example 4 (7.8 g, 53.0 mmol) at room temperature, and the mixture was stirred at the same temperature for 30 minutes. The compound obtained in Reference Example 2 (13.5 g, 53.0 mmol) was added, and the mixture was stirred for 30 minutes, and further stirred at 100° C. for 3 hours. After the reaction mixture was cooled to room temperature, water was added to the reaction mixture, and the mixture was subjected to extraction twice with ethyl acetate. The organic layer thus obtained was washed with water and a 10% aqueous solution of sodium chloride, and then was dried over anhydrous sodium sulfate. The solvent was distilled off under reduced pressure, and the resulting residue was purified by silica gel column chromatography (hexane:ethyl acetate=95:5→85:15, v/v) to give the title compound (14.7 g, yield: 76%).

$^1$H-NMR (400 MHz, CDCl$_3$) δ ppm:
7.96 (1H, t, J=8 Hz), 7.90 (1H, dd, J=8, 2 Hz), 7.84 (1H, dd, J=11, 2 Hz), 5.92 (1H, t, J=7 Hz), 2.21 (3H, s), 2.16-2.08 (2H, m), 1.62 (9H, s), 1.05 (3H, t, J=7 Hz);
MS (FAB) m/z: 365 [M+H]$^+$.

Reference Example 6 tert-Butyl 2-fluoro-4-{5-[(1S)-1-hydroxypropyl]-1,2,4-oxadiazol-3-yl}benzoate

[Chemical Formula 8]

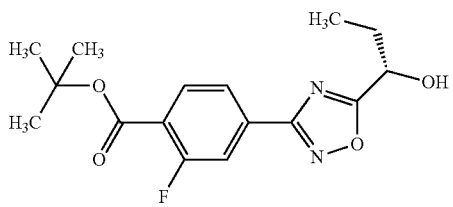

Potassium carbonate (8.4 g, 61 mmol) was added to a methanol (100 mL) solution of the compound obtained in Reference Example 5 (14.7 g, 40.3 mmol) under ice cooling, and the mixture was stirred at the same temperature for 30 minutes. 2 N Hydrochloric acid was added to the reaction mixture at the same temperature until a pH value of 6.0 was obtained. The reaction mixture was subjected to extraction twice with ethyl acetate, and the organic layer thus obtained was washed with water and brine, and then was dried over anhydrous sodium sulfate. The solvent was distilled off under reduced pressure, and the resulting residue was purified by silica gel column chromatography (hexane:ethyl acetate=95:5→80:20, v/v) to give the title compound (12.9 g, yield: 84%).

$^1$H-NMR (400 MHz, CDCl$_3$) δ ppm:
7.97 (1H, t, J=8 Hz), 7.91 (1H, d, J=8 Hz), 7.85 (1H, d, J=11 Hz), 4.98 (1H, q, J=6 Hz), 2.54 (1H, brs), 2.14-1.96 (2H, m), 1.62 (9H, s), 1.08 (3H, t, J=7 Hz);
MS (FAB) m/z: 323 [M+H]$^+$.

Reference Example 7 tert-Butyl 4-(5-{(1R)-1-[4-(cyclopropylcarbonyl)phenoxy]propyl}-1,2,4-oxadiazol-3-yl)-2-fluorobenzoate

[Chemical Formula 9]

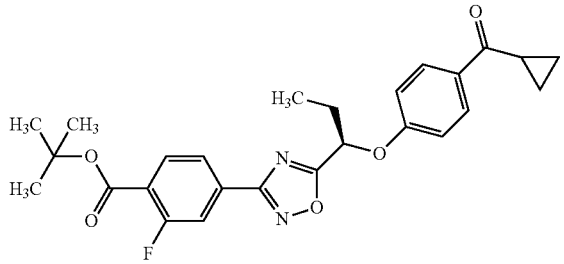

di-Tert-butyl azodicarboxylate (260 mg, 1.11 mmol) and triphenylphosphine (300 mg, 1.11 mmol) were added to a tetrahydrofuran solution (10 mL) of the compound obtained in Reference Example 6 (300 mg, 0.931 mmol) and the compound obtained in Reference Example 3 (150 mg, 0.925 mmol) at room temperature, and the mixture was stirred at the same temperature for one hour. The solvent was distilled off under reduced pressure, and the resulting residue was purified by silica gel column chromatography (hexane:ethyl acetate=95:5→80:20, v/v) to give the title compound (236 mg, yield: 55%).

$^1$H-NMR (400 MHz, CDCl$_3$) δ ppm:
8.00-7.94 (3H, m), 7.90-7.87 (1H, m), 7.84-7.81 (1H, m), 7.06-7.04 (2H, m), 5.52 (1H, dd, J=7, 6 Hz), 2.63-2.57 (1H, m), 2.34-2.25 (2H, m), 1.61 (9H, s), 1.21-1.18 (2H, m), 1.14 (3H, t, J=7 Hz), 1.01-0.98 (2H, m);
MS (FAB$^+$) m/z: 466 [M+H]$^+$.

Reference Example 8

4-(5-{(1R)-1-[4-(Cyclopropylcarbonyl)phenoxy]propyl}-1,2,4-oxadiazol-3-yl)-2-fluorobenzoic acid

[Chemical Formula 10]

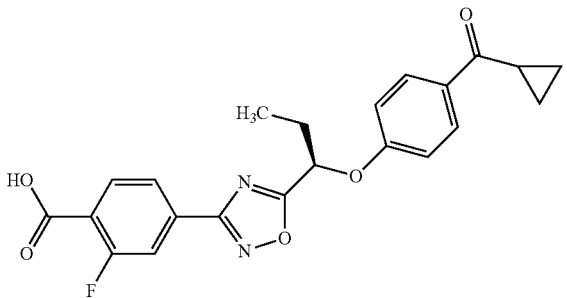

Trifluoroacetic acid (10 mL) was added to a dichloromethane (1 mL) solution of the compound obtained in Reference Example 7 (236 mg, 0.506 mmol) at room temperature, and the mixture was stirred for 40 minutes. The solvent was distilled off under reduced pressure, and the resulting residue was washed with isopropyl ether. Thus, the title compound (195 mg, yield: 94%) was obtained.

$^1$H-NMR (400 MHz, CDCl$_3$) δ ppm:
8.14 (1H, t, J=8 Hz), 8.01-7.89 (4H, m), 7.04 (2H, dd, J=7, 2 Hz), 5.54 (1H, dd, J=7, 6 Hz), 2.63-2.57 (1H, m), 2.35-2.21 (2H, m), 1.22-1.18 (2H, m), 1.15 (3H, q, J=5 Hz), 1.02-0.99 (2H, m);
MS (FAB) m/z: 411 [M+H]$^+$.

Reference Example 9 tert-Butyl 2-fluoro-4-{5-[(1S)-1-hydroxyethyl]-1,2,4-oxadiazol-3-yl}benzoate

[Chemical Formula 11]

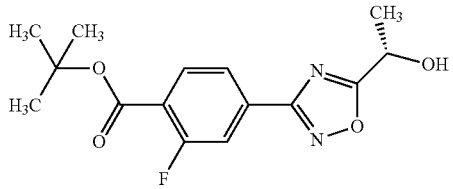

1-Hydroxybenzotriazole monohydrate (16.7 g, 109 mmol) and N-(3-dimethylaminopropyl)-N'-ethylcarbodiimide (41.8 g, 218 mmol) were added to a dimethylformamide (540 mL) solution of (2S)-2-acetoxy propionic acid (14.4 g, 109 mmol) at room temperature, and the mixture was stirred at the same temperature for 30 minutes. The compound obtained in Reference Example 2 (27.7 g, 109 mmol) was added, and the mixture was stirred for 10 minutes, and further stirred at 90° C. for 3 hours. After the reaction mixture was cooled to room temperature, water and a 10% aqueous solution of sodium chloride were added to the reaction mixture, and the mixture was subjected to extraction twice with ethyl acetate. The organic layer thus obtained was washed with a 10% aqueous solution of sodium chloride and a saturated aqueous solution of sodium hydrogen carbonate, and then was dried over anhydrous sodium sulfate. The solvent was distilled off under reduced pressure, and the resulting residue was purified by silica gel column chromatography (hexane:ethyl acetate=95:5→85:15, v/v).

Potassium carbonate (12.7 g, 91.6 mmol) was added to a methanol (360 mL) solution of the obtained tert-butyl 4-{5-[(1S)-1-acetoxyethyl]-1,2,4-oxadiazol-3-yl}-2-fluorobenzoate (32.1 g, 91.6 mmol) under ice cooling, and the mixture was stirred at the same temperature for 30 minutes. 2 N Hydrochloric acid was added to the reaction mixture at the same temperature until a pH value of 6.0 was obtained, and the solvent was distilled off under reduced pressure. Water was added to the resulting residue, and the mixture was subjected to extraction twice with ethyl acetate. The organic layer thus obtained was dried over anhydrous sodium sulfate. The solvent was distilled off under reduced pressure, and the resulting residue was solidified by using hexane. Thus, the title compound (26.4 g, yield: 93%) was obtained.

$^1$H-NMR (400 MHz, CDCl$_3$) δ ppm:
7.97 (1H, t, J=8 Hz), 7.90 (1H, d, J=8 Hz), 7.84 (1H, d, J=5 Hz), 5.18 (1H, q, J=7 Hz), 1.73 (4H, d, J=7 Hz), 1.60 (9H, s);
MS (FAB) m/z: 309 [M+H]$^+$.

Reference Example 10 tert-Butyl 4-(5-{(1R)-1-[4-(cyclopropylcarbonyl)phenoxy]ethyl}-1,2,4-oxadiazol-3-yl)-2-fluorobenzoate

[Chemical Formula 12]

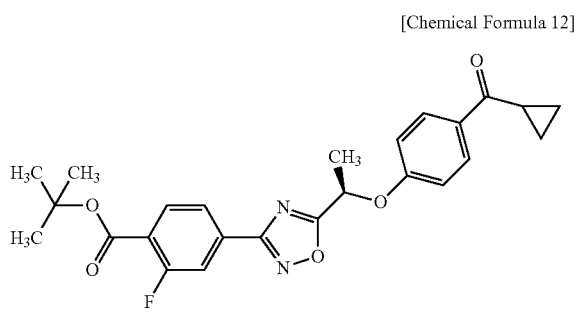 [SMILES: C[C@@H](Oc1ccc(C(=O)C2CC2)cc1)c1nc(-c2ccc(C(=O)OC(C)(C)C)c(F)c2)no1]

Triphenylphosphine (5.62 g, 21.4 mmol) and di-tert-butyl azodicarboxylate (4.93 g, 21.4 mmol) were added to a tetrahydrofuran solution (190 mL) of the compound obtained in Reference Example 9 (6.00 g, 19.5 mmol) and the compound obtained in Reference Example 3 (3.47 g, 21.4 mmol) at room temperature, and the mixture was stirred at the same temperature for 40 minutes. The solvent was distilled off under reduced pressure, and the resulting residue was purified by silica gel column chromatography (hexane:ethyl acetate=95:5→75:25, v/v) to give the title compound (7.65 g, yield: 87%).
$^1$H-NMR (400 MHz, CDCl$_3$) δ ppm:
8.02-7.94 (3H, m), 7.89 (1H, d, J=8 Hz), 7.83 (1H, d, J=8 Hz), 7.05 (2H, d, J=8 Hz), 5.75 (1H, q, J=7 Hz), 2.63-2.59 (1H, m), 1.92 (3H, d, J=4 Hz), 1.48 (9H, s), 1.20 (2H, m), 1.01-0.99 (2H, m).

Reference Example 11

4-(5-{(1R)-1-[4-(Cyclopropylcarbonyl)phenoxy]ethyl}-1,2,4-oxadiazol-3-yl)-2-fluorobenzoic acid

[Chemcial Formula 13]

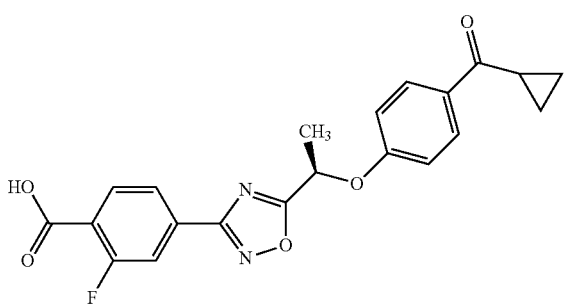

A dichloromethane (20 mL) solution of trifluoroacetic acid (20 mL) was added to a dichloromethane (40 mL) solution of the compound obtained in Reference Example 10 (7.65 g, 16.9 mmol) at room temperature, and the mixture was stirred for one hour. The solvent was distilled off under reduced pressure, and the resulting residue was solidified by using hexane:ethyl acetate (4:1, v/v). Thus, the title compound (4.90 g, yield: 73%) was obtained.
$^1$H-NMR (400 MHz, CDCl$_3$) δ ppm:
8.14 (1H, t, J=8 Hz), 8.01 (2H, d, J=9 Hz), 7.98-7.96 (1H, m), 7.93-7.90 (1H, m), 7.06 (2H, d, J=9 Hz), 5.76 (1H, q, J=7 Hz), 2.64-2.57 (1H, m), 1.92 (3H, d, J=7 Hz), 1.23-1.18 (2H, m), 1.03-0.98 (2H, m);
MS (FAB) m/z: 397 [M+H]$^+$.

Reference Example 12

(4S)-4-aminodihydrofuran-2(3H)-one

[Chemical Formula 14]

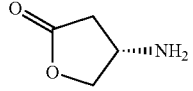

20 w % palladium on carbon (60 mg) was added to a tetrahydrofuran (6 mL) solution of benzyl[(3S)-5-oxotetrahydrofuran-3-yl]carbamate (600 mg, 2.55 mmol) at room temperature, and the mixture was stirred for 2 hours under hydrogen flow. Methanol (60 μL) was added at room temperature, and the mixture was stirred for 2 hours under hydrogen flow. The insoluble material was removed by filtration through Celite. Thus, a tetrahydrofuran solution of the title compound was obtained.

Reference Example 13

(3S,4S)-3-amino-4-hydroxydihydrofuran-2-(3H)-one

[Chemical Formula 15]

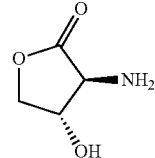

20% palladium hydroxide on carbon (9.5 mg) was added to an ethanol (5.0 mL) solution of benzyl[(3S,4S)-4-hydroxy-2-oxotetrahydrofuran-3-yl]carbamate (Bioorg. Med. Chem. Lett. 2002, 12, 325-328.) (94.8 mg, 0.377 mmol) at room temperature, and the mixture was stirred at the same temperature for 3.5 hours under hydrogen flow. The insoluble material was removed by filtration through Celite. The solvent was distilled off under reduced pressure. Thus, the crude title compound (44.2 mg) was obtained.

Reference Example 14

(3S,4R)-3-amino-4-hydroxydihydrofuran-2-(3H)-one

[Chemical Formula 16]

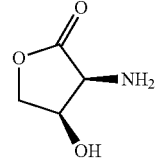

20% palladium hydroxide on carbon (12.2 mg) was added to an ethanol (5.0 mL) solution of benzyl[(3S,4R)-4-hydroxy-2-oxotetrahydrofuran-3-yl]carbamate (Bioorg. Med. Chem. Lett. 2002, 12, 325-328.) (122 mg, 0.486 mmol) at room temperature, and the mixture was stirred at the same temperature for 3.5 hours under hydrogen flow. The insoluble material was removed by filtration through Celite. The solvent was distilled off under reduced pressure. Thus, the crude title compound (85.4 mg) was obtained.

Example 1

4-(5-{(1R)-1-[4-(cyclopropylcarbonyl)phenoxy]propyl}-1,2,4-oxadiazol-3-yl)-2-fluoro-N-[(3S,4R)-4-hydroxytetrahydrofuran-3-yl]benzamide, and 4-(5-{(1R)-1-[4-(cyclopropylcarbonyl)phenoxy]propyl}-1,2,4-oxadiazol-3-yl)-2-fluoro-N-[(3R,4S)-4-hydroxytetrahydrofuran-3-yl]benzamide

[Chemical Formula 17]

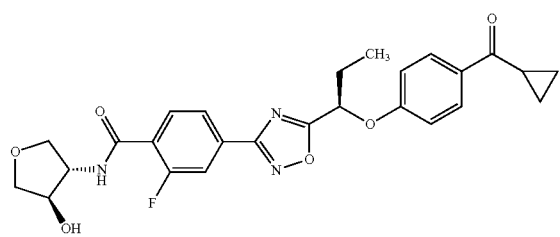

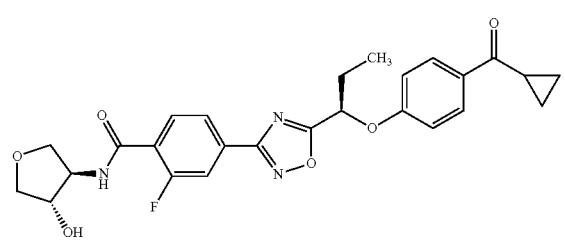

1-Hydroxybenzotriazole monohydrate (153 mg, 1.00 mmol) and N-(3-dimethylaminopropyl)-N'-ethylcarbodiimide hydrochloride (383 mg, 2.00 mmol) were added to an N,N-dimethylformamide (4 mL) solution of the compound obtained in Reference Example 8 (410 mg, 1.00 mmol) at room temperature. The mixture was stirred at the same temperature for 30 minutes. Subsequently, (3RS,4SR)-4-aminotetrahydrofuran-3-ol (J. Org. Chem. 1997, 62, 4197.) (155 mg, 1.50 mmol) was added, and the mixture was further stirred at the same temperature for 30 minutes. Water and a saturated aqueous solution of sodium hydrogen carbonate were added to the reaction mixture, and the mixture was subjected to extraction three times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (hexane:ethyl acetate=50:50→0:100, v/v) to give the title compounds (241 mg, yield: 49%).

$^1$H-NMR (400 MHz, CDCl$_3$) δ ppm:
8.20 (1H, t, J=8 Hz), 8.04-7.95 (3H, m), 7.87 (1H, d, J=12 Hz), 7.04 (2H, d, J=9 Hz), 6.97-6.87 (1H, m), 5.53 (1H, t, J=6 Hz), 4.44-4.37 (2H, m), 4.22 (1H, dd, J=8, 6 Hz), 4.15 (1H, dd, J=9, 6 Hz), 3.84-3.72 (2H, m), 3.19-3.16 (1H, m), 2.63-2.55 (1H, m), 2.35-2.18 (2H, m), 1.23-1.10 (5H, m), 1.03-0.96 (2H, m);

MS (FAB) m/z: 496 [M+H]$^+$.

Example 2

4-(5-{(1R)-1-[4-(cyclopropylcarbonyl)phenoxy]ethyl}-1,2,4-oxadiazol-3-yl)-2-fluoro-N-[(3R,4S)-4-hydroxytetrahydrofuran-3-yl]benzamide

[Chemical Formula 18]

1-Hydroxybenzotriazole monohydrate (153 mg, 1.00 mmol) and N-(3-dimethylaminopropyl)-N'-ethylcarbodiimide hydrochloride (383 mg, 2.00 mmol) were added to an N,N-dimethylformamide (5 mL) solution of the compound obtained in Reference Example 11 (396 mg, 1.00 mmol) at room temperature. The mixture was stirred at the same temperature for 30 minutes. Subsequently, (3S,4R)-4-aminotetrahydrofuran-3-ol (J. Org. Chem. 1997, 62, 4197.) (155 mg, 1.50 mmol) was added, and the mixture was further stirred at the same temperature for 30 minutes. Water was added to the reaction mixture, and the mixture was subjected to extraction three times with ethyl acetate. The organic layer thus obtained was washed with a saturated aqueous solution of sodium hydrogen carbonate and a 10% aqueous solution of sodium chloride, and then was dried over anhydrous sodium sulfate. The solvent was distilled off under reduced pressure, and the resulting residue was purified by silica gel column chromatography (hexane:ethyl acetate=50:50→0:100, v/v) to give the title compound (393 mg, yield: 82%).

$^1$H-NMR (400 MHz, CDCl$_3$) δ ppm:
8.19 (1H, t, J=8 Hz), 8.02-7.97 (3H, m), 7.87 (1H, dd, J=12, 1 Hz), 7.05 (2H, d, J=9 Hz), 6.95-6.87 (1H, m), 5.76 (1H, q, J=7 Hz), 4.44-4.37 (2H, m), 4.21 (1H, dd, J=10, 5 Hz), 4.15 (1H, dd, J=10, 5 Hz), 3.82 (1H, dd, J=10, 3 Hz), 3.75 (1H, dd, J=10, 3 Hz), 3.32 (1H, d, J=2 Hz), 2.63-2.57 (1H, m), 1.92 (3H, d, J=7 Hz), 1.22-1.19 (2H, m), 1.03-0.98 (2H, m);

MS (FAB) m/z: 482 [M+H]$^+$.

Example 3

4-(5-{(1R)-1-[4-(cyclopropylcarbonyl)phenoxy]ethyl}-1,2,4-oxadiazol-3-yl)-2-fluoro-N-[(3S,4R)-4-hydroxytetrahydrofuran-3-yl]benzamide

[Chemical Formula 19]

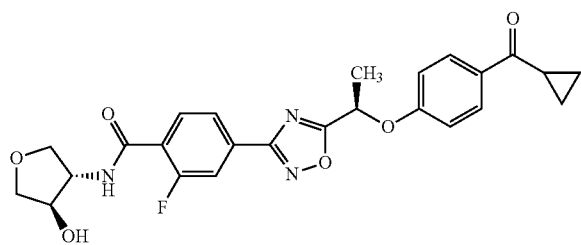

1-Hydroxybenzotriazole monohydrate (153 mg, 1.00 mmol) and N-(3-dimethylaminopropyl)-N'-ethylcarbodiimide hydrochloride (383 mg, 2.00 mmol) were added to an N,N-dimethylformamide (5 mL) solution of the compound obtained in Reference Example 11 (396 mg, 1.00 mmol) at room temperature. The mixture was stirred at the same temperature for 30 minutes. Subsequently, (3R,4S)-4-aminotetrahydrofuran-3-ol (J. Org. Chem. 1997, 62, 4197.) (155 mg, 1.50 mmol) was added, and the mixture was further stirred at the same temperature for 30 minutes. Water was added to the reaction mixture, and the mixture was subjected to extraction three times with ethyl acetate. The organic layer thus obtained was washed with a saturated aqueous solution of sodium hydrogen carbonate and a 10% aqueous solution of sodium chloride, and then was dried over anhydrous sodium sulfate. The solvent was distilled off under reduced pressure, and the resulting residue was purified by silica gel column chromatography (hexane:ethyl acetate=50:50→0:100, v/v) to give the title compound (410 mg, yield: 85%).
$^1$H-NMR (400 MHz, CDCl$_3$) δ ppm:
8.20 (1H, t, J=8 Hz), 8.04-7.97 (3H, m), 7.87 (1H, dd, J=12, 1 Hz), 7.06 (2H, d, J=9 Hz), 6.97-6.87 (1H, m), 5.76 (1H, q, J=7 Hz), 4.46-4.38 (2H, m), 4.22 (1H, dd, J=10, 5 Hz), 4.15 (1H, dd, J=10, 5 Hz), 3.82 (1H, dd, J=10, 3 Hz), 3.75 (1H, dd, J=10, 4 Hz), 3.21-3.18 (1H, m), 2.65-2.56 (1H, m), 1.92 (3H, d, J=7 Hz), 1.24-1.18 (2H, m), 1.04-0.98 (2H, m);
MS (FAB) m/z: 482 [M+H]$^+$.

Example 4

4-(5-{(1R)-1-[4-(cyclopropylcarbonyl)phenoxy]propyl}-1,2,4-oxadiazol-3-yl)-2-fluoro-N-[(3R)-2-oxotetrahydrofuran-3-yl]benzamide

[Chemical Formula 20]

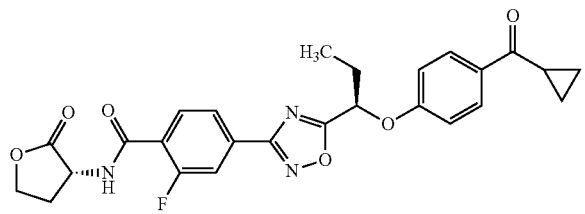

1-Hydroxybenzotriazole monohydrate (153 mg, 1.00 mmol) and N-(3-dimethylaminopropyl)-N'-ethylcarbodiimide hydrochloride (383 mg, 2.00 mmol) were added to an N,N-dimethylformamide (5 mL) solution of the compound obtained in Reference Example 8 (410 mg, 1.00 mmol) at room temperature. The mixture was stirred at the same temperature for 30 minutes. Subsequently, (3R)-3-aminodihydrofuran-2(3H)-one hydrochloride (206 mg, 1.50 mmol) and triethylamine (140 μL, 1.00 mmol) were added, and the mixture was further stirred at the same temperature for 30 minutes. Water and a saturated aqueous solution of sodium hydrogen carbonate were added to the reaction mixture, and the mixture was subjected to extraction three times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (hexane:ethyl acetate=95:5→50:50, v/v) to give the title compound (382 mg, yield: 77%).
$^1$H-NMR (400 MHz, CDCl$_3$) δ ppm:
8.21 (1H, t, J=8 Hz), 8.03-7.96 (3H, m), 7.89 (1H, dd, J=13, 1 Hz), 7.42-7.24 (1H, m), 7.04 (2H, d, J=9 Hz), 5.53 (1H, t, J=7 Hz), 4.74-4.71 (1H, m), 4.56 (1H, t, J=9 Hz), 4.41-4.34 (1H, m), 3.01-2.94 (1H, m), 2.63-2.57 (1H, m), 2.40-2.20 (3H, m), 1.22-1.18 (2H, m), 1.15 (3H, t, J=7 Hz), 1.02-0.97 (2H, m);
MS (FAB) m/z: 494 [M+H]$^+$.

Example 5

4-(5-{(1R)-1-[4-(cyclopropylcarbonyl)phenoxy]propyl}-1,2,4-oxadiazol-3-yl)-2-fluoro-N-[(3S)-2-oxotetrahydrofuran-3-yl]benzamide

[Chemical Formula 21]

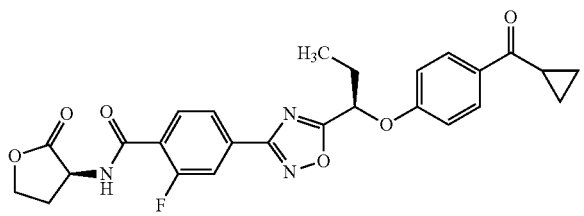

1-Hydroxybenzotriazole monohydrate (153 mg, 1.00 mmol) and N-(3-dimethylaminopropyl)-N'-ethylcarbodiimide hydrochloride (383 mg, 2.00 mmol) were added to an N,N-dimethylformamide (5 mL) solution of the compound obtained in Reference Example 8 (410 mg, 1.00 mmol) at room temperature. The mixture was stirred at the same temperature for 30 minutes. Subsequently, (3S)-3-aminodihydrofuran-2(3H)-one hydrobromide (270 mg, 1.50 mmol) and triethylamine (140 μL, 1.00 mmol) were added, and the mixture was further stirred at the same temperature for 30 minutes. Water and a saturated aqueous solution of sodium hydrogen carbonate were added to the reaction mixture, and the mixture was subjected to extraction three times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (hexane:ethyl acetate=95:5→50:50, v/v) to give the title compound (390 mg, yield: 79%).
$^1$H-NMR (400 MHz, CDCl$_3$) δ ppm:
8.22 (1H, t, J=8 Hz), 8.03-7.96 (3H, m), 7.89 (1H, dd, J=13, 1 Hz), 7.42-7.37 (1H, m), 7.04 (2H, d, J=9 Hz), 5.53 (1H, t, J=7 Hz), 4.74-4.71 (1H, m), 4.56 (1H, t, J=9 Hz), 4.41-4.34 (1H, m), 3.01-2.94 (1H, m), 2.63-2.57 (1H, m), 2.40-2.20 (3H, m), 1.22-1.18 (2H, m), 1.15 (3H, t, J=7 Hz), 1.02-0.97 (2H, m);
MS (FAB) m/z: 494 [M+H]$^+$.

Example 6

4-(5-{(1R)-1-[4-(cyclopropylcarbonyl)phenoxy]propyl}-1,2,4-oxadiazol-3-yl)-2-fluoro-N-[(3S)-5-oxotetrahydrofuran-3-yl]benzamide

[Chemical Formula 22]

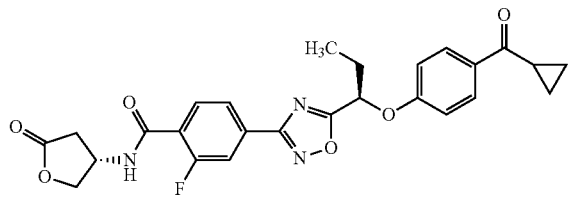

1-Hydroxybenzotriazole monohydrate (81.3 mg, 0.531 mmol) and N-(3-dimethylaminopropyl)-N'-ethylcarbodiimide hydrochloride (204 mg, 1.06 mmol) were added to an N,N-dimethylformamide (3 mL) solution of the compound obtained in Reference Example 8 (218 mg, 0.531 mmol) at room temperature. The mixture was stirred at the same temperature for 30 minutes. Subsequently, a tetrahydrofuran solution of the (4S)-4-aminodihydrofuran-2(3H)-one obtained in Reference Example 12 (76 mg, 0.797 mmol) was added, and the mixture was further stirred at the same temperature for 30 minutes. Water and a saturated aqueous solution of sodium hydrogen carbonate were added to the reaction mixture, and the mixture was subjected to extraction three times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (hexane:ethyl acetate=95:5→50:50, v/v) to give the title compound (88.7 mg, yield: 34%).

$^1$H-NMR (400 MHz, CDCl$_3$) δ ppm:
8.20 (1H, t, J=8 Hz), 8.03-7.97 (3H, m), 7.89 (1H, dd, J=13, 2 Hz), 7.05-6.96 (3H, m), 5.53 (1H, t, J=7 Hz), 4.98-4.88 (1H, m), 4.66 (1H, dd, J=10, 6 Hz), 4.37 (1H, dd, J=10, 4 Hz), 3.01 (1H, dd, J=18, 8 Hz), 2.67-2.55 (2H, m), 2.35-2.19 (2H, m), 1.23-1.10 (5H, m), 1.02-0.97 (2H, m);
MS (FAB) m/z: 494 [M+H]$^+$.

Example 7

4-(5-{(1R)-1-[4-(cyclopropylcarbonyl)phenoxy]propyl}-1,2,4-oxadiazol-3-yl)-2-fluoro-N-[(3R)-2-oxopyrrolidin-3-yl]benzamide

[Chemical Formula 23]

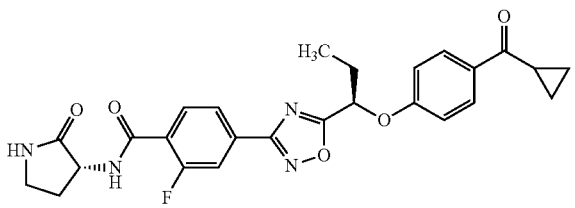

1-Hydroxybenzotriazole monohydrate (129 mg, 0.840 mmol) and N-(3-dimethylaminopropyl)-N'-ethylcarbodiimide hydrochloride (242 mg, 1.26 mmol) were added to an N,N-dimethylformamide (4 mL) solution of the compound obtained in Reference Example 8 (345 mg, 0.840 mmol) at room temperature. The mixture was stirred at the same temperature for 30 minutes. Subsequently, (3R)-3-aminopyrrolidin-2-one (101 mg, 1.01 mmol) was added, and the mixture was further stirred at the same temperature for 30 minutes. Water and a saturated aqueous solution of sodium hydrogen carbonate were added to the reaction mixture, and the mixture was subjected to extraction five times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (ethyl acetate:methanol=100:0→90:10, v/v) to give the title compound (285 mg, yield: 69%).

$^1$H-NMR (400 MHz, CDCl$_3$) δ ppm:
8.21 (1H, t, J=8 Hz), 8.03-7.96 (3H, m), 7.87 (1H, dd, J=12, 1 Hz), 7.34-7.27 (1H, m), 7.04 (2H, d, J=9 Hz), 5.98-5.90 (1H, m), 5.53 (1H, t, J=6 Hz), 4.62-4.55 (1H, m), 3.50-3.45 (2H, m), 2.97-2.89 (1H, m), 2.63-2.57 (1H, m), 2.35-2.19 (2H, m), 2.18-2.05 (1H, m), 1.23-1.17 (2H, m), 1.14 (3H, t, J=7 Hz), 1.04-0.97 (2H, m);
MS (ESI) m/z: 493 [M+H]$^+$.

Example 8

4-(5-{(1R)-1-[4-(cyclopropylcarbonyl)phenoxy]propyl}-1,2,4-oxadiazol-3-yl)-2-fluoro-N-[(3S)-2-oxopyrrolidin-3-yl]benzamide

[Chemical Formula 24]

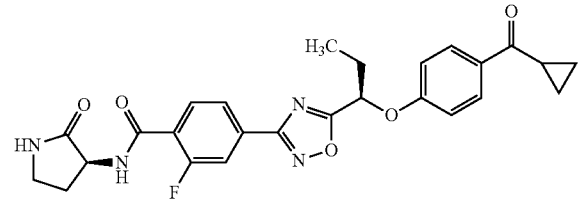

1-Hydroxybenzotriazole monohydrate (129 mg, 0.840 mmol) and N-(3-dimethylaminopropyl)-N'-ethylcarbodiimide hydrochloride (242 mg, 1.26 mmol) were added to an N,N-dimethylformamide (4 mL) solution of the compound obtained in Reference Example 8 (345 mg, 0.840 mmol) at room temperature. The mixture was stirred at the same temperature for 30 minutes. Subsequently, (3S)-3-aminopyrrolidin-2-one (101 mg, 1.01 mmol) was added, and the mixture was further stirred at the same temperature for 30 minutes. Water and a saturated aqueous solution of sodium hydrogen carbonate were added to the reaction mixture, and the mixture was subjected to extraction five times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (ethyl acetate:methanol=100:0→90:10, v/v) to give the title compound (225 mg, yield: 54%).

¹H-NMR (400 MHz, CDCl₃) δ ppm:
8.21 (1H, t, J=8 Hz), 8.03-7.97 (3H, m), 7.88 (1H, dd, J=12, 1 Hz), 7.34-7.27 (1H, m), 7.03 (2H, d, J=9 Hz), 5.81-5.75 (1H, m), 5.53 (1H, t, J=6 Hz), 4.63-4.55 (1H, m), 3.51-3.42 (2H, m), 2.96-2.88 (1H, m), 2.64-2.56 (1H, m), 2.35-2.19 (2H, m), 2.18-2.05 (1H, m), 1.23-1.17 (2H, m), 1.14 (3H, t, J=7 Hz), 1.03-0.97 (2H, m);
MS (ESI) m/z: 493 [M+H]⁺.

Example 9

4-(5-{(1R)-1-[4-(cyclopropylcarbonyl)phenoxy]propyl}-1,2,4-oxadiazol-3-yl)-2-fluoro-N-[(3S,4S)-4-hydroxy-2-oxotetrahydrofuran-3-yl]benzamide

[Chemical Formula 25]

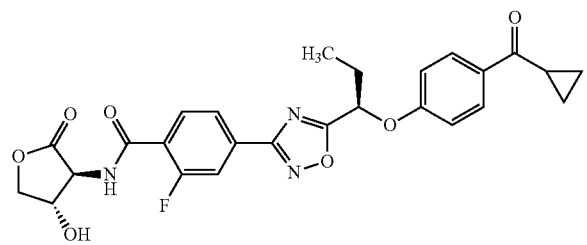

1-Hydroxybenzotriazole monohydrate (46.1 mg, 0.301 mmol) and N-(3-dimethylaminopropyl)-N'-ethylcarbodiimide hydrochloride (57.7 mg, 0.301 mmol) were added to an N,N-dimethylformamide (0.5 mL) solution of the 4-(5-{(1R)-1-[4-(cyclopropylcarbonyl)phenoxy]propyl}-1,2,4-oxadiazol-3-yl)-2-fluorobenzoic acid synthesized in Reference Example 8 (103 mg, 0.252 mmol) at room temperature, and the mixture was stirred at the same temperature for 30 minutes. Subsequently, an N,N-dimethylformamide (1.0 mL) solution of the (3S,4S)-3-amino-4-hydroxydihydrofuran-2-(3H)-one synthesized in Reference Example 13 (44.2 mg) was added, and the mixture was further stirred at the same temperature for 30 minutes. Water was added to the reaction mixture, and the mixture was subjected to extraction twice with ethyl acetate. The organic layer thus obtained was washed with a saturated aqueous solution of sodium hydrogen carbonate and brine, and then was dried over anhydrous sodium sulfate. The solvent was distilled off under reduced pressure, and the resulting residue was purified by silica gel column chromatography (hexane:ethyl acetate=70:30→30:70, v/v) to give the title compound (48.5 mg, yield: 38%).
¹H-NMR (500 MHz, CDCl₃) δ ppm:
8.21 (1H, t, J=8 Hz), 8.06-7.97 (3H, m), 7.92 (1H, dd, J=13, 1 Hz), 7.64-7.57 (1H, m), 7.04 (2H, d, J=9 Hz), 5.54 (1H, dd, J=7, 6 Hz), 5.40-5.38 (1H, m), 4.69-4.60 (2H, m), 4.57-4.51 (1H, m), 4.21-4.14 (1H, m), 2.63-2.57 (1H, m), 2.36-2.20 (2H, m), 1.22-1.18 (2H, m), 1.15 (3H, t, J=7 Hz), 1.03-0.97 (2H, m);
MS (ES) m/z: 510 [M+H]⁺.

Example 10

4-(5-{(1R)-1-[4-(cyclopropylcarbonyl)phenoxy]ethyl}-1,2,4-oxadiazol-3-yl)-2-fluoro-N-[(3R)-2-oxopyrrolidin-3-yl]benzamide

[Chemical Formula 26]

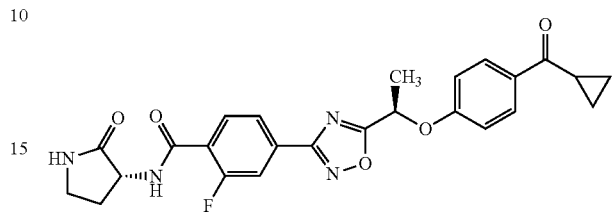

1-Hydroxybenzotriazole monohydrate (137 mg, 0.896 mmol) and N-(3-dimethylaminopropyl)-N'-ethylcarbodiimide hydrochloride (258 mg, 1.34 mmol) were added to an N,N-dimethylformamide (4 mL) solution of the compound obtained in Reference Example 11 (355 mg, 0.896 mmol) at room temperature. The mixture was stirred at the same temperature for 30 minutes. Subsequently, (3R)-3-aminopyrrolidin-2-one (108 mg, 1.07 mmol) was added, and the mixture was further stirred at the same temperature for 30 minutes. Water was added to the reaction mixture, and the mixture was subjected to extraction five times with ethyl acetate. The organic layer thus obtained was washed with a saturated aqueous solution of sodium hydrogen carbonate and a 10% aqueous solution of sodium chloride, and then was dried over anhydrous sodium sulfate. The solvent was distilled off under reduced pressure, and the resulting residue was purified by silica gel column chromatography (ethyl acetate:methanol=100:0→90:10, v/v) to give the title compound (14.3 mg, yield: 3%).
¹H-NMR (400 MHz, CDCl₃) δ ppm:
8.21 (1H, t, J=8 Hz), 8.02-7.97 (3H, m), 7.87 (1H, dd, J=12, 1 Hz), 7.34-7.30 (1H, m), 7.05 (2H, d, J=9 Hz), 5.78-5.74 (2H, m), 4.62-4.54 (1H, m), 3.49-3.45 (2H, m), 2.98-2.89 (1H, m), 2.64-2.57 (1H, m), 2.17-2.07 (1H, m), 1.92 (3H, d, J=7 Hz), 1.22-1.18 (2H, m), 1.03-0.97 (2H, m);
MS (ESI) m/z: 479 [M+H]⁺.

Example 11

4-(5-{(1R)-1-[4-(cyclopropylcarbonyl)phenoxy]ethyl}-1,2,4-oxadiazol-3-yl)-2-fluoro-N-[(3S)-2-oxopyrrolidin-3-yl]benzamide

[Chemical Formula 27]

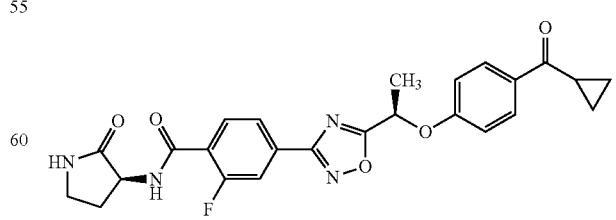

1-Hydroxybenzotriazole monohydrate (137 mg, 0.896 mmol) and N-(3-dimethylaminopropyl)-N'-ethylcarbodiimide hydrochloride (258 mg, 1.34 mmol) were added to an N,N-dimethylformamide (4 mL) solution of the compound obtained in Reference Example 11 (355 mg, 0.896 mmol) at room temperature. The mixture was stirred at the same temperature for 30 minutes. Subsequently, (3S)-3-aminopyrrolidin-2-one (108 mg, 1.07 mmol) was added, and the mixture was further stirred at the same temperature for 30 minutes. Water was added to the reaction mixture, and the mixture was subjected to extraction five times with ethyl acetate. The organic layer thus obtained was washed with a saturated aqueous solution of sodium hydrogen carbonate and a 10% aqueous solution of sodium chloride, and then was dried over anhydrous sodium sulfate. The solvent was distilled off under reduced pressure, and the resulting residue was purified by silica gel column chromatography (ethyl acetate:methanol=100:0→90:10, v/v) to give the title compound (257 mg, yield: 60%).

$^1$H-NMR (400 MHz, CDCl$_3$) δ ppm:

8.21 (1H, t, J=8 Hz), 8.08-7.96 (3H, m), 7.87 (1H, dd, J=12, 1 Hz), 7.38-7.30 (1H, m), 7.06 (2H, d, J=9 Hz), 5.90-5.75 (2H, m), 4.64-4.55 (1H, m), 3.53-3.43 (2H, m), 2.98-2.89 (1H, m), 2.68-2.57 (1H, m), 2.19-2.07 (1H, m), 1.92 (3H, d, J=7 Hz), 1.25-1.17 (2H, m), 1.09-0.96 (2H, m);

MS(ESI) m/z: 479 [M+H]$^+$.

Example 12

4-(5-{(1R)-1-[4-(cyclopropylcarbonyl)phenoxy]propyl}-1,2,4-oxadiazol-3-yl)-2-fluoro-N-[(3S,4R)-4-hydroxy-2-oxotetrahydrofuran-3-yl]benzamide

[Chemical Formula 28]

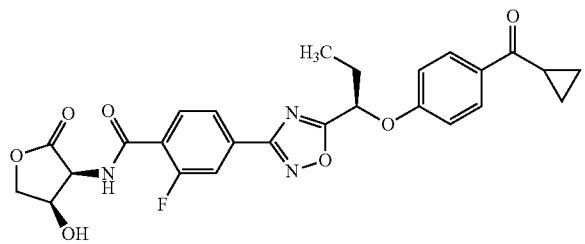

1-Hydroxybenzotriazole monohydrate (44.6 mg, 0.291 mmol) and N-(3-dimethylaminopropyl) -N'-ethylcarbodiimide hydrochloride (55.8 mg, 0.291 mmol) were added to an N,N-dimethylformamide (0.5 mL) solution of the 4-(5-{(1R)-1-[4 -(cyclopropylcarbonyl) phenoxy]propyl}-1,2,4-oxadiazol-3-yl)-2-fluorobenzoic acid synthesized in Reference Example 8 (99.6 mg, 0.243 mmol) at room temperature, and the mixture was stirred at the same temperature for 30 minutes. Subsequently, an N,N-dimethylformamide (1.0 mL) solution of the crude (3S,4R)-3-amino-4-hydroxydihydrofuran-2-(3H)-one synthesized in Reference Example 14 (85.4 mg) was added, and the mixture was further stirred at the same temperature for 30 minutes. Water was added to the reaction mixture, and the mixture was subjected to extraction twice with ethyl acetate. The organic layer thus obtained was washed with a saturated aqueous solution of sodium hydrogen carbonate and brine, and then was dried over anhydrous sodium sulfate. The solvent was distilled off under reduced pressure, and the resulting residue was purified by silica gel column chromatography (hexane:ethyl acetate=70:30→30:70, v/v) to give the title compound (22.5 mg, yield: 18%).

$^1$H-NMR (500 MHz, CDCl$_3$) δ ppm:

8.20 (1H, t, J=8 Hz), 8.02-7.97 (3H, m), 7.89 (1H, d, J=12 Hz), 7.35-7.28 (1H, m), 7.04 (2H, d, J=9 Hz), 5.53 (1H, dd J=7, 6 Hz), 4.09-4.86 (2H, m), 4.54 (1H, dd, J=11, 1 Hz), 4.49 (1H, d, J=11 Hz), 2.64-2.56 (2H, m), 2.36-2.20 (2H, m), 1.22-1.17 (2H, m), 1.15 (3H, t, J=7 Hz), 1.02-0.98 (2H, m);

MS (ES) m/z: 510 [M+H]$^+$.

Example 13

4-(5-{(1R)-1-[4-(cyclopropylcarbonyl)phenoxy]ethyl}-1,2,4-oxadiazol-3-yl)-2-fluoro-N-[(3R,4R)-4-hydroxytetrahydrofuran-3-yl]benzamide

[Chemical Formula 29]

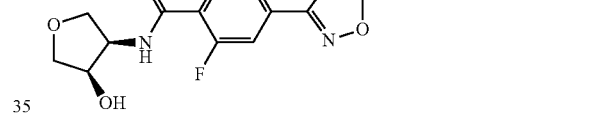

1-Hydroxybenzotriazole monohydrate (132 mg, 0.864 mmol) and N-(3-dimethylaminopropyl)-N'-ethylcarbodiimide hydrochloride (249 mg, 1.30 mmol) were added to an N,N-dimethylformamide (4 mL) solution of the compound obtained in Reference Example 11 (343 mg, 0.864 mmol) at room temperature. The mixture was stirred at the same temperature for 30 minutes. Subsequently, (3R,4R)-4-aminotetrahydrofuran-3-ol (J. Org. Chem. 1997, 62, 4197.) (181 mg, 1.30 mmol) and triethylamine (181 μL, 1.30 mmol) were added, and the mixture was further stirred at the same temperature for 30 minutes. Water and a saturated aqueous solution of sodium hydrogen carbonate were added to the reaction mixture, and the mixture was subjected to extraction three times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (hexane:ethyl acetate=50:50→0:100, v/v) to give the title compound (240 mg, yield: 58%).

$^1$H-NMR (400 MHz, CDCl$_3$) δ ppm:

8.20 (1H, t, J=8 Hz), 8.02-7.96 (3H, m), 7.86 (1H, dd, J=12, 1 Hz), 7.47-7.42 (1H, m), 7.05 (2H, d, J=9 Hz), 5.76 (1H, q, J=7 Hz), 4.70-4.63 (1H, m), 4.54-4.49 (1H, m), 4.22 (1H, dd, J=9, 8 Hz), 4.07 (1H, dd, J=10, 4 Hz), 3.87 (1H, dd, J=10, 2 Hz), 3.72 (1H, dd, J=9, 7 Hz), 2.63-2.57 (1H, m), 2.29-2.23 (1H, m), 1.92 (3H, d, J=7 Hz), 1.22-1.18 (2H, m), 1.03-0.98 (2H, m);

MS (FAB) m/z: 482 [M+H]$^+$.

Example 14

4-(5-{(1R)-1-[4-(cyclopropylcarbonyl)phenoxy]ethyl}-1,2,4-oxadiazol-3-yl)-2-fluoro-N-[(3S,4S)-4-hydroxytetrahydrofuran-3-yl]benzamide

[Chemical Formula 30]

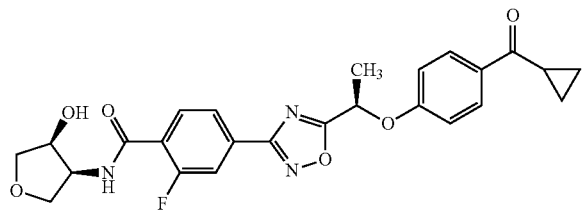

1-Hydroxybenzotriazole monohydrate (132 mg, 0.864 mmol) and N-(3-dimethylaminopropyl)-N'-ethylcarbodiimide hydrochloride (249 mg, 1.30 mmol) were added to an N,N-dimethylformamide (4 mL) solution of the compound obtained in Reference Example 11 (343 mg, 0.864 mmol) at room temperature. The mixture was stirred at the same temperature for 30 minutes. Subsequently, (3S,4S)-4-aminotetrahydrofuran-3-ol (J. Org. Chem. 1997, 62, 4197.) (181 mg, 1.30 mmol) and triethylamine (181 μL, 1.30 mmol) were added, and the mixture was further stirred at the same temperature for 30 minutes. Water and a saturated aqueous solution of sodium hydrogen carbonate were added to the reaction mixture, and the mixture was subjected to extraction three times with ethyl acetate. The organic layer thus obtained was washed with a 10% aqueous solution of sodium chloride, and then was dried over anhydrous sodium sulfate. The solvent was distilled off under reduced pressure, and the resulting residue was purified by silica gel column chromatography (hexane:ethyl acetate=50:50→0:100, v/v) to give the title compound (275 mg, yield: 66%).

$^1$H-NMR (400 MHz, CDCl$_3$) δ ppm:
8.21 (1H, t, J=8 Hz), 8.02-7.96 (3H, m), 7.87 (1H, dd, J=12, 1 Hz), 7.47-7.42 (1H, m), 7.05 (2H, d, J=9 Hz), 5.76 (1H, q, J=7 Hz), 4.70-4.63 (1H, m), 4.54-4.49 (1H, m), 4.23 (1H, dd, J=9, 8 Hz), 4.07 (1H, dd, J=10, 4 Hz), 3.88 (1H, dd, J=10, 2 Hz), 3.72 (1H, dd, J=9, 7 Hz), 2.63-2.57 (1H, m), 2.15 (1H, d, J=5 Hz), 1.92 (3H, d, J=7 Hz), 1.22-1.18 (2H, m), 1.03-0.98 (2H, m);
MS (FAB) m/z: 482 [M+H]$^+$.

FORMULATION EXAMPLE 5 g of each of the compounds obtained in the Examples, 90 g of lactose, 34 g of corn starch, 20 g of crystalline cellulose, and 1 g of magnesium stearate are mixed with a blender, and then the mixture is tableted with a tableting machine. Thereby, tablets are obtained.

Test Example 1

Mouse oGTT (Oral Glucose Tolerance Test

A dosing preparation (1 mg/mL of each compound) was produced by suspending in a 0.5 w/v % methyl cellulose solution and then grinding in an agate mortar. Male C57/BL6J mice (Charles River Laboratories Japan, Inc.) were purchased at 6 to 8 weeks of age, and then used at 9 to 13 weeks of age. The mice were fasted between 17:00 and 18:00 one day before the test day, and the test was started after 16 to 17 hours of fasting. Five mice were used for each group. After collecting blood from the tail vein, a suspension of the compound was administered orally at a dosage of 10 mg/kg. The 0.5 w/v % methyl cellulose solution was administered to a negative control group. Blood was collected from the tail vein 25 minutes after administration of the compound, and then 30 w/v % glucose solution was administered orally at a volume of 10 mL/kg 30 minutes after the compound administration. Blood was collected from the tail vein 15, 30, 60 and 120 minutes after the glucose administration. Each of the blood samples was centrifuged to obtain the plasma, and the plasma glucose level (mg/dL) was measured with a glucose analyzer (Glucoloader-GXT, A&T Corp.). The plasma glucose AUC (mg/dL·min) in each mouse was calculated using the plasma glucose levels at 5 minutes before and 15, 30, 60 and 120 minutes after the glucose administration. The arithmetic mean of the AUC was calculated for each group and the percentage decrease in plasma glucose AUC (%) compared with the negative control group was calculated as an index of the efficacy.

As a result, the compounds of Examples 3, 8, 10, and 13 showed a 5% or more to less than 15% percentage decrease in plasma glucose AUC (%) and the compounds of Examples 1, 2, 4 to 7, 9, 11, 12, and 14 showed a 15% or more percentage decrease in plasma glucose AUC.

Test Example 2

Rat oGTT and Measurement of Plasma Compound Concentration

Each compound is suspended in vehicle (0.5 w/v % methyl cellulose or 20 w/v % cyclodextrin solution) at a concentration of 1 to 10 mg/mL. When assessing the dose dependency, the prepared suspension is diluted with the above-described vehicle in a stepwise fashion. Male Zucker fatty rats (Charles River Laboratories Japan, Inc.) or Zucker diabetic fatty (ZDF) rats (Charles River Laboratories Japan, Inc.) are used at 10 to 18 weeks of age. Two days before the oGTT, plasma glucose and insulin concentrations and body weight are measured, and rats are equally allocated to each group (n=5 to 8) based on these parameters. The rats are fasted from around 15:00 one day before the oGTT day. On the oGTT day, the suspension prepared by the method described above is administered orally to the rats at a volume of 1 to 5 mL/kg, and 30 minutes after the dosing, 25 to 50 w/v % glucose solution is administered orally at a volume of 4 mL/kg. Blood is collected from the tail vein before the administration of the compound, 5 minutes before the administration of glucose, and 30, 60, 120, and 180 minutes after the administration of glucose. The obtained blood samples are centrifuged to separate the plasma, and the plasma glucose level is measured with a glucose analyzer (Glucoloader-GXT, A&T Corp.). The plasma glucose AUC in each rat is calculated using the plasma glucose levels before and after the glucose administration. The arithmetic mean of the AUC is calculated in each group and the percentage decrease in the AUC (%) compared with the vehicle-administered group is calculated as an index of the efficacy.

The plasma samples obtained by the method described above are used for measurement of the plasma concentration of the test compound. In order to quantify the plasma concentration of the test compound, blood is additionally collected 4 to 8 hours and 24 hours after the administration of the compound. The plasma is subjected to protein removal, and applied to a liquid chromatography/mass analyzer to quantify the plasma concentration of the test compound.

Test Example 3

Assessment for the Protective Effect on Pancreatic β Cells

The protective effect of the test compound on pancreatic β cells can be confirmed with reference to the method described in Junko Ogawa, et al., Life Sciences, Vol. 65, No. 12, pp. 1287-1296 (1999).

INDUSTRIAL APPLICABILITY

The compounds of the present invention or pharmaceutically acceptable salts thereof are capable of treating and/or preventing type 1 diabetes, type 2 diabetes, gestational diabetes, hyperglycemia due to other factors, impaired glucose tolerance, diabetes-associated diseases, diabetic complications and the like, and are therefore useful as an active ingredient of a pharmaceutical composition for protecting β cells or the pancreas.

The invention claimed is:
1. A compound represented by general formula (I):

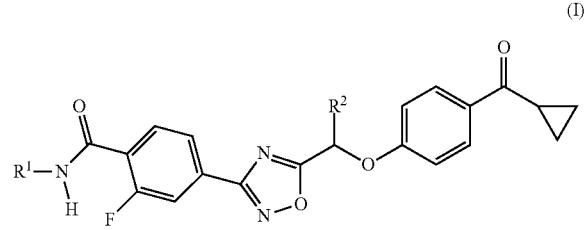

wherein
$R^1$ represents

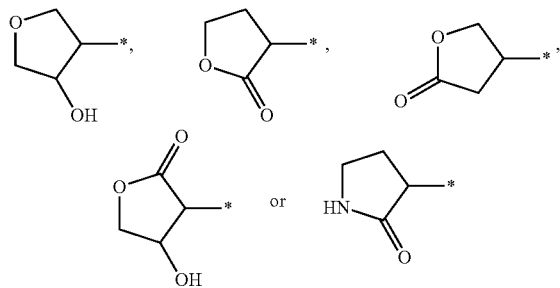

* represents the point of attachment to the nitrogen atom, and
$R^2$ represents a methyl group or an ethyl group;
or a pharmaceutically acceptable salt thereof.
2. A compound selected from the group consisting of the following compounds:
4-(5-{(1R)-1-[4-(cyclopropylcarbonyl)phenoxy]propyl}-1,2,4-oxadiazol-3-yl)-2-fluoro -N-[(3S,4R)-4-hydroxytetrahydrofuran-3-yl]benzamide;
4-(5-{(1R)-1-[4-(cyclopropylcarbonyl)phenoxy]propyl}1,2,4-oxadiazol-3-yl)-2-fluoro -N-[(3R,4S)-4-hydroxytetrahydrofuran-3-yl]benzamide;
4-(5-{(1R)-1-[4-(cyclopropylcarbonyl)phenoxy]ethyl}-1,2,4-oxadiazol-3-yl)-2-fluoro-N-[(3R,4S)-4-hydroxytetrahydrofuran-3-yl]benzamide;
4-(5-{(1R)-1-[4 -(cyclopropylcarbonyl)phenoxy]ethyl}-1,2,4-oxadiazol-3-yl)-2-fluoro-N-[(3S,4R)-4-hydroxytetrahydrofuran-3-yl]benzamide;
4-(5-{(1R)-1-[4-(cyclopropylcarbonyl)phenoxy]propyl}-1,2,4-oxadiazol-3-yl)-2-fluoro-N-[(3R)-2-oxotetrahydrofuran-3-yl]benzamide;
4-(5-{(1R)-1-[4-(cyclopropylcarbonyl)phenoxy]propyl}-1,2,4-oxadiazol-3-yl)-2-fluoro-N-[(3S)-2-oxotetrahydrofuran-3-yl]benzamide;
4-(5-{(1R)-1-[4-(cyclopropylcarbonyl)phenoxy]propyl}-1,2,4-oxadiazol-3-yl)-2-fluoro-N-[(3S)-5-oxotetrahydrofuran-3-yl]benzamide;
4-(5-{(1R)-1-[4-(cyclopropylcarbonyl)phenoxy]propyl}-1,2,4-oxadiazol-3-yl)-2-fluoro-N-[(3R)-2-oxopyrrolidin-3-yl]benzamide;
4-(5-{(1R)-1-[4-(cyclopropylcarbonyl)phenoxy]propyl}-1,2,4-oxadiazol-3-yl)-2-fluoro-N-[(3S)-2-oxopyrrolidin-3-yl]benzamide;
4-(5-{(1R)-1[4-(cyclopropylcarbonyl)phenoxy]propyl}--1,2,4-oxadiazol-3-yl)-2-fluoro-N-[(3S,4S)-4-hydroxy-2-oxotetrahydrofuran-3-yl]benzamide;
4-(5-{(1R)-1[4-(cyclopropylcarbonyl)phenoxy]ethyl}-1,2,4-oxadiazol-3-yl)-2-fluoro-[(3R)-2-oxopyrrolidin-3-yl]benzamide;
4-(5-{(1R)-1[4-(cyclopropylcarbonyl)phenoxy]ethyl}-1,2,4-oxadiazol-3-yl)-2-fluoro-N-[(3S)-2-oxopyrrolidin-3-yl]benzamide;
4-(5-{(1R)-1[4-(cyclopropylcarbonyl)phenoxy]propyl}-1,2,4-oxadiazol-3-yl)-2-fluoro-N-[(3S,4R)-4-hydroxy-2-oxotetrahydrofuran-3-yl]benzamide;
4-(5-{(1R)-1-[4-(cyclopropylcarbonyl)phenoxy]ethyl}-1,2,4-oxadiazol-3-yl)-2-fluoro-N-[(3R,4R)-4-hydroxytetrahydrofuran-3-yl]benzamide; and
4-(5-{(1R)-1-[4-(cyclopropylcarbonyl)phenoxyl]ethyl}-1,2,4-oxadiazol-3-yl)-2-fluoro-N-[(3S,4S)-4-hydroxytetrahydrofuran-3 -yl]benzamide;
or a pharmaceutically acceptable salt thereof.
3. A pharmaceutical composition comprising an excipient and, as an active ingredient, a compound according to claim 1 or a pharmaceutically acceptable salt thereof.
4. A method for treating type 1diabetes, type 2 diabetes, or obesity, the method comprising administering to a mammal a compound according to claim 1 or a pharmaceutically acceptable salt thereof.
5. A method according to claim 4, wherein the mammal is a human being.
6. A method according to claim 4, wherein the disease is type 1 diabetes.
7. A method for treating type 1 diabetes, type 2 diabetes, or obesity, the method comprising administering to a mammal a compound according to claim 2 or a pharmaceutically acceptable salt thereof.
8. A method according to claim 7, wherein the mammal is a human being.
9. A method according to claim 7, wherein the disease is type 1 diabetes.
10. A method for protecting β-cell or the pancreas, the method comprising administering to a mammal a compound according to claim 1 or a pharmaceutically acceptable salt thereof.
11. A method according to claim 10, wherein the mammal is a human being.

12. A method for protecting β-cell or the pancreas, the method comprising administering to a mammal a compound according to claim 2 or a pharmaceutically acceptable salt thereof.

13. A method according to claim 12, wherein the mammal is a human being.

14. A pharmaceutical composition comprising an excipient and, as an active ingredient, a compound according to claim 2 or a pharmaceutically acceptable salt thereof.

\* \* \* \* \*